United States Patent
Guillemont et al.

(10) Patent No.: US 9,573,942 B2
(45) Date of Patent: Feb. 21, 2017

(54) HIV INHIBITING 5-AMIDO SUBSTITUTED PYRIMIDINES

(71) Applicant: Janssen Sciences Ireland UC, Little Island (IE)

(72) Inventors: Jerôme Emile Georges Guillemont, Andé (FR); Mikaël Paugam, Heudreville sur Eure (FR); Bruno François Marie Delest, Rouen (FR)

(73) Assignee: Janssen Sciences Ireland UC, Little Island, Cork County (IE)

( * ) Notice: Subject to any disclaimer, the term of this patent is extended or adjusted under 35 U.S.C. 154(b) by 0 days.

(21) Appl. No.: 14/566,400

(22) Filed: Dec. 10, 2014

(65) Prior Publication Data

US 2015/0099749 A1    Apr. 9, 2015

Related U.S. Application Data

(63) Continuation of application No. 12/294,692, filed as application No. PCT/EP2007/053111 on Mar. 30, 2007, now Pat. No. 8,933,089.

(30) Foreign Application Priority Data

Mar. 30, 2006 (EP) ..................................... 06112044

(51) Int. Cl.

| A61K 31/505 | (2006.01) |
|---|---|
| C07D 239/02 | (2006.01) |
| C07D 417/12 | (2006.01) |
| C07D 239/48 | (2006.01) |
| C07D 401/12 | (2006.01) |
| C07D 405/12 | (2006.01) |
| C07D 409/12 | (2006.01) |

(52) U.S. Cl.
CPC ........... *C07D 417/12* (2013.01); *C07D 239/48* (2013.01); *C07D 401/12* (2013.01); *C07D 405/12* (2013.01); *C07D 409/12* (2013.01)

(58) Field of Classification Search
CPC ... C07D 239/48; C07D 401/12; C07D 417/12; C07D 409/12; C07D 405/12
USPC .................................. 544/323, 325; 514/272
See application file for complete search history.

(56) References Cited

U.S. PATENT DOCUMENTS

| 3,459,731 | A | 8/1969 | Gramera et al. |
|---|---|---|---|
| 6,593,326 | B1 | 7/2003 | Bradbury et al. |
| 7,504,396 | B2 | 3/2009 | Nunes et al. |
| 7,531,548 | B2 | 5/2009 | Guillemont et al. |
| 8,933,089 | B2 | 1/2015 | Guillemont et al. |
| 2003/0036543 | A1 | 2/2003 | Bebbington |
| 2005/0209221 | A1 | 9/2005 | Nunes et al. |
| 2008/0262007 | A1 | 10/2008 | Guillemont et al. |
| 2009/0181993 | A1 | 7/2009 | Guillemont et al. |
| 2010/0016317 | A1 | 1/2010 | Guillemont et al. |
| 2010/0168104 | A1 | 7/2010 | Guillemont et al. |
| 2010/0261722 | A1 | 10/2010 | Guillemont et al. |

FOREIGN PATENT DOCUMENTS

| EA | 002973 B1 | 12/2002 |
|---|---|---|
| EP | 0834507 B1 | 4/1998 |
| SU | 290582 | 11/1970 |
| WO | WO-97/18839 A1 | 5/1997 |
| WO | WO-99/50250 A1 | 10/1999 |
| WO | WO-99/50256 A1 | 10/1999 |
| WO | WO-00/27825 A1 | 5/2000 |
| WO | WO-00/39101 A1 | 7/2000 |
| WO | WO-01/85700 A2 | 11/2001 |
| WO | WO-03/016306 A1 | 2/2003 |
| WO | WO-03/063794 A2 | 8/2003 |
| WO | WO-03/099820 A1 | 12/2003 |
| WO | WO-2004/046143 A1 | 6/2004 |
| WO | WO-2004/080980 A1 | 9/2004 |
| WO | WO-2005/009443 A1 | 2/2005 |
| WO | WO-2006/035067 A2 | 4/2006 |
| WO | WO-2006/035069 A1 | 4/2006 |
| WO | WO-2007/113254 A1 | 10/2007 |
| WO | WO-2008/080964 A1 | 7/2008 |

(Continued)

OTHER PUBLICATIONS

U.S. Appl. No. 11/576,315: Non-Final Office Action dated Oct. 4, 2010.
U.S. Appl. No. 11/575,818: Final Office Action dated Feb. 2, 2011.
U.S. Appl. No. 11/576,315: Final Office Action dated Feb. 2, 2011.
U.S. Appl. No. 12/521,189: Final Office Action dated Apr. 10, 2012.
U.S. Appl. No. 11/575,818: Non-Final Office Action dated Aug. 5, 2010.
U.S. Appl. No. 12/294,692: Non-Final Office Action dated Nov. 26, 2010.
U.S. Appl. No. 12/294,692: Final Office Action dated May 13, 2011.
U.S. Appl. No. 12/521,189: Non-Final Office Action dated Sep. 23, 2011. U.S. Appl. No. 12/521,379: Non-Final Office Action dated Sep. 26, 2011.

(Continued)

*Primary Examiner* — Shengjun Wang
(74) *Attorney, Agent, or Firm* — Johnson & Johnson; Robert DeBerardine

(57) ABSTRACT

This invention concerns pyrimidine derivatives of formula

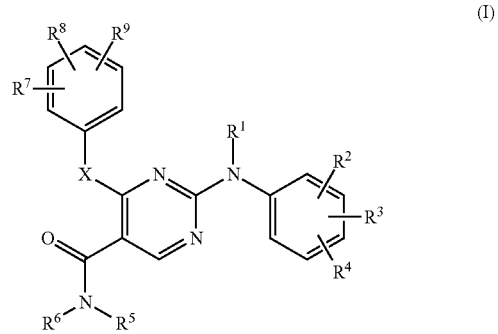

(I)

having HIV (Human Immunodeficiency Virus) replication inhibiting properties, the preparation thereof and pharmaceutical compositions comprising these compounds.

11 Claims, No Drawings

(56) References Cited

FOREIGN PATENT DOCUMENTS

WO     WO-2008/080965 A1     7/2008

OTHER PUBLICATIONS

U.S. Appl. No. 12/294,692: Non-Final Office Action dated Aug. 1, 2013.
U.S. Appl. No. 12/294,692: Final Office Action dated Nov. 13, 2013.
Ludovici et al., "Evolution of Anti-HIV Drug Candidates. Part 3: Diarylpyrimidine (DAPY) Analogues", *Bioorganic & Medicinal Chemistry Letters*, vol. 11, pp. 2235-2239, 2001.
Nogradi, M., "Dimethyl-β-Cyclodextrin," *Drugs of the Future*, 9(8):577-578, 1984.
PCT/EP2005/054930: International Search Report dated Jun. 20, 2006.
PCT/EP2005/054932: International Search Report dated Sep. 12, 2005.
PCT/EP2007/053111: International Search Report dated Aug. 9, 2007.
PCT/EP2007/064605: International Search Report dated May 6, 2008.
PCT/EP2007/064606: International Search Report dated Jul. 14, 2008.
Russian Patent Application No. 2008143001: Decision of Grant received Nov. 8, 2012 (including translation).
Russian Patent Application No. 2008143001: Office Action received Nov. 25, 2011 (including translation).
Vippagunta, S. et al., "Crystalline solids,"*Advanced Drug Delivery Reviews*, 2001; 48: 3-26.

HIV INHIBITING 5-AMIDO SUBSTITUTED PYRIMIDINES

This application is a continuation of U.S. application Ser. No. 12/294,692, filed Sep. 26, 2008, now U.S. Pat. No. 8,933,089 (issued Jan. 13, 2015), which is a national stage application of Patent Application No. PCT/EP2007/053111, filed Mar. 30, 2007, which application claims priority from European Patent Application No. 06112044.0, filed Mar. 30, 2006, the contents of which are hereby incorporated by reference in their entirety.

This invention concerns 5-amido substituted pyrimidines having HIV (Human Immunodeficiency Virus) replication inhibiting properties, the preparation thereof and pharmaceutical compositions comprising these compounds.

Resistance of the HIV virus against currently available HIV drugs continues to be a major cause of therapy failure. This has led to the introduction of combination therapy of two or more anti-HIV agents usually having a different activity profile. Significant progress was made by the introduction of HAART therapy (Highly Active Anti-Retroviral Therapy), which has resulted in a significant reduction of morbidity and mortality in HIV patient populations treated therewith. HAART involves various combinations of nucleoside reverse transcriptase inhibitors (NRTIs), non-nucleoside reverse transcriptase inhibitors (NNRTIs) and protease inhibitors (PIs). But even these multidrug therapies do not completely eliminate HIV and long-term treatment often leads to multidrug resistance. In many cases, resistant virus is carried over to newly infected individuals, resulting in limited therapy options for such drug-naive patients.

Therefore there is a continued need for new combinations of active ingredients that are effective against HIV. New types of anti-HIV agents, differing in chemical structure and activity profile are needed in new types of combination therapy. Finding such active ingredients therefore is a highly desirable goal to achieve.

The present invention is aimed at providing particular novel series of pyrimidine derivatives having HIV replication inhibiting properties. WO 99/50250, WO 00/27825 and WO 01/85700 disclose certain substituted aminopyrimidines having HIV replication inhibiting properties.

The compounds of the invention differ from prior art compounds as regards their structure as well as their pharmacological profile. It has been found that the introduction of certain substituents in the 5-position of specifically substituted pyrimidines results in compounds the compounds not only acting favorably in terms of their capability to inhibit the replication of Human Immunodeficiency Virus (HIV), but also by their improved ability to inhibit the replication of mutant strains, in particular strains which have become resistant to one or more known NNRTI drugs, which strains are referred to as drug or multidrug resistant HIV strains.

Thus in one aspect, the present invention concerns compounds of formula

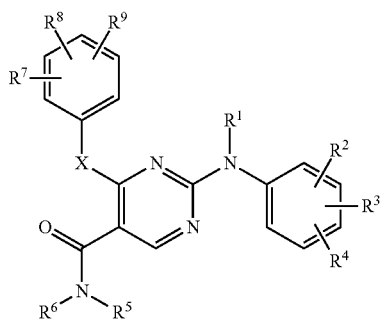

(I)

the stereochemically isomeric forms, the pharmaceutically acceptable addition salts thereof, the pharmaceutically acceptable hydrates or solvates thereof, the N-oxides thereof, wherein each $R^1$ independently is hydrogen; aryl; formyl; $C_{1-6}$alkylcarbonyl; $C_{1-6}$alkyl; $C_{1-6}$alkyloxycarbonyl;

$R^2$, $R^3$, $R^7$ and $R^8$ independently are hydrogen; hydroxy; halo; $C_{3-7}$cycloalkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; polyhalo$C_{1-6}$alkyloxy; —C(=O)$R^{10}$; $C_{1-6}$ alkyl optionally substituted with halo, cyano, or —C(=O)$R^{10}$; $C_{2-6}$alkenyl optionally substituted with halo, cyano or —C(=O)$R^{10}$; $C_{2-6}$alkynyl optionally substituted with halo, cyano, or —C(=O)$R^{10}$;

$R^4$ and $R^9$ independently are hydroxy; halo; $C_{3-7}$cycloalkyl; $C_{1-6}$alkyloxy; carboxyl; $C_{1-6}$ alkyloxycarbonyl; formyl; cyano; nitro; amino; mono- or di($C_{1-6}$ alkyl)amino; polyhalo$C_{1-6}$alkyl; polyhalo$C_{1-6}$alkyloxy; —C(=O)$R^{10}$; —S(=O)$_r R^{10}$; —NH—S(=O)$_r R^{10}$; —NHC(=O)H; —C(=O)NHNH$_2$; —NHC(=O)$R^{10}$; Het; —Y-Het; $C_{1-12}$alkyl optionally substituted with halo, cyano, amino, mono- or di($C_{1-6}$ alkyl)amino, —C(=O)—$R^{10}$, Het or with $C_{1-6}$alkyloxy; $C_{2-12}$alkenyl optionally substituted with halo, cyano, amino, mono- or di($C_{1-6}$ alkyl)amino, —C(=O)—$R^{10}$, Het or with $C_{1-6}$alkyloxy; $C_{2-12}$alkynyl optionally substituted with halo, cyano, amino, mono- or di($C_{1-6}$alkyl)amino, —C(=O)—$R^{10}$, Het, or with $C_{1-6}$alkyloxy;

$R^5$ is $C_{3-7}$cycloalkyl; $C_{1-6}$alkyloxy; aryl; Het; $C_{1-6}$alkyl substituted with a radical selected from hydroxy, $C_{1-6}$alkyloxy, cyano, amino, mono- and di-$C_{1-6}$alkylamino, $C_{1-6}$alkylcarbonylamino, aryl, Het, dioxolanyl optionally substituted with one or two $C_{1-6}$ alkyl radicals, tetrahydrofuranyl, pyrrolidinyl, piperidinyl, morpholinyl, piperazinyl, piperazinyl optionally substituted with $C_{1-6}$alkyl or $C_{1-6}$alkylcarbonyl, $C_{1-6}$ alkyloxycarbonyl, aryl$C_{1-6}$alkyloxycarbonyl, and $C_{3-7}$cycloalkyl; or $R^5$ is $C_{1-6}$alkyl substituted with two $C_{1-6}$alkyloxy radicals;

$R^6$ is hydrogen or $C_{1-6}$alkyl; or $R^5$ and $R^6$ taken together with the nitrogen atom to which they are attached form pyrrolidinyl; piperidinyl; morpholinyl; piperazinyl; piperazinyl optionally substituted with $C_{1-6}$alkyl or $C_{1-6}$alkylcarbonyl;

each $R^{10}$ independently is $C_{1-6}$alkyl, amino, mono- or di($C_{1-6}$ alkyl)amino, or polyhalo-$C_{1-6}$ alkyl;

X is —NR$^1$—, —O—, —C(=O)—, —CH$_2$—, —CHOH—, —S—, —S(=O)r-;

each Y independently is —NR$^1$—, —O—, —C(=O)—, —S—, —S(=O)r-;

each r independently is 1 or 2;

each Het independently is pyridyl, thienyl, furanyl, oxazolyl, thiazolyl, thiadiazolyl, oxadiazolyl, isoxazolyl, isothiazolyl, imidazolyl, triazolyl, tetrazolyl, pyrazolyl, quinolinyl, benzothienyl, benzofuranyl, benzoxazolyl, benzothiazolyl; which each may optionally be substituted with one or two substituents each independently selected from $C_{1-6}$alkyl, halo, hydroxy, cyano, $C_{1-6}$alkyloxy, $C_{2-12}$alkenyl substituted with halo, hydroxy or with cyano;

each aryl independently is phenyl or phenyl substituted with one, two, three, four or five substituents each independently selected from halo, hydroxy, mercapto, $C_{1-6}$alkyl, $C_{2-6}$alkenyl, $C_{2-6}$alkynyl, hydroxy$C_{1-6}$alkyl, amino$C_{1-6}$ alkyl, mono and di($C_{1-6}$alkyl)-amino$C_{1-6}$alkyl, $C_{1-6}$alkylcarbonyl, $C_{3-7}$cycloalkyl, $C_{1-6}$alkyloxy, phenyl$C_{1-6}$ alkyloxy, $C_{1-6}$ alkyloxycarbonyl, aminosulfonyl, $C_{1-6}$ alkylthio, cyano, nitro, polyhalo$C_{1-6}$alkyl, polyhalo$C_{1-6}$ alkyloxy, aminocarbonyl, phenyl, Het, and —Y-Het.

As used hereinbefore or hereinafter $C_{1-4}$alkyl as a group or part of a group defines straight or branched chain saturated hydrocarbon radicals having from 1 to 4 carbon atoms such as methyl, ethyl, 1-propyl, 2-propyl, 1-butyl, 2-butyl, 2-methylpropyl, t.butyl; $C_{1-6}$alkyl as a group or part of a group defines straight or branched chain saturated hydrocarbon radicals having from 1 to 6 carbon atoms such as the group defined for $C_{1-4}$alkyl and 1-pentyl, 2-pentyl, 1-hexyl, 2-hexyl, 3-hexyl, 2-methylbutyl, 3-methylpentyl and the like; $C_{1-2}$alkyl defines methyl or ethyl; $C_{3-7}$cycloalkyl is generic to cyclopropyl, cyclobutyl, cyclopentyl, cyclohexyl and cycloheptyl. Preferred amongst $C_{1-6}$alkyl are $C_{1-4}$alkyl or $C_{1-2}$alkyl. Preferred amongst $C_{3-7}$cycloalkyl are cyclopentyl and cyclohexyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 1-pentenyl, 2-pentenyl, 3-pentenyl, 2-methyl-1-butenyl, 1-hexenyl, 2-hexenyl, 3-hexenyl, 4-hexenyl, 2-methyl-2-pentenyl, 1,2-dimethyl-1-butenyl and the like. Preferred are $C_{2-6}$alkenyls having one double bond. Of interest amongst $C_{2-6}$alkenyl radicals are the $C_{2-4}$alkyl radicals. The term "$C_{3-6}$alkenyl" is as $C_{2-6}$ alkenyl but is limited to unsaturated hydrocarbon radicals having from 3 to 6 carbon atoms. In the instances where a $C_{3-6}$alkenyl is linked to a heteroatom, the carbon atom linked to the heteroatom by preference is saturated. The term "$C_{2-12}$alkenyl" is as $C_{2-6}$alkenyl but has from 2 to 12 carbon atoms and includes the $C_{2-6}$alkenyl radicals and the higher homologs such as 1-heptenyl, 2-heptenyl, 3-heptenyl, 1-methyl-1-hexenyl, 1,2-dimethyl1-pentenyl, 2-methyl-1-hexenyl, 2-ethyl-2-pentenyl, 3-propyl-2-hexenyl, 1-octenyl, 2-octenyl, 1-nonenyl, 1-decenyl, 1-undecenyl, 1-dodecenyl and the like. Preferred amongst $C_{2-12}$alkenyl are the $C_{2-6}$alkenyl radicals.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-methyl-2-propynyl, 2-pentynyl, 3-pentynyl, 2-hexynyl, 3-hexynyl, 4-hexynyl, 2-methyl-2-butynyl, 2-methyl-2-pentynyl and the like. Preferred are $C_{2-6}$alkynyls having one triple bond. Of interest amongst $C_{2-6}$alkynyl radicals are the $C_{2-4}$alkyl radicals. The term "$C_{3-6}$alkynyl" is as $C_{2-6}$alkynyl but is limited to unsaturated hydrocarbon radicals having from 3 to 6 carbon atoms. In the instances where a $C_{3-6}$alkynyl is linked to a heteroatom, the carbon atom linked to the heteroatom by preference is saturated. The term "$C_{2-12}$alkynyl" is as $C_{2-6}$alkynyl but has from 2 to 12 carbon atoms and includes the $C_{2-6}$alkynyl radicals and the higher homologs such as 1-heptynyl, 2-heptynyl, 1-octynyl, 2-octynyl, 1-nonynyl, 1-decynyl, 1-undecynyl, 1-dodecynyl and the like. Preferred amongst $C_{2-12}$alkynyl are the $C_{2-6}$alkynyl radicals.

As used herein before, the term (=O) forms a carbonyl moiety when attached to a carbon atom, a sulfoxide moiety when attached to a sulfur atom and a sulfonyl moiety when two of said terms are attached to a sulfur atom.

The terms carboxyl, carboxy or hydroxycarbonyl refer to a group —COOH.

The term "halo" is generic to fluoro, chloro, bromo or iodo.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoro-ethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

Any of the heterocycles mentioned in the definitions of Het is meant to comprise any isomer such as for example oxadiazole may be 1,2,4-oxadiazole, 1,3,4-oxadiazole, or 1,2,3-oxadiazole; likewise for thiadiazole which may be 1,2,4-thiadiazole, 1,3,4-thia-diazole, or 1,2,3-thiadiazole; similarly, imidazole may be 1H-imidazole or 3H-imidazole.

Whenever a radical occurs in the definition of the compounds of formula (I) or in any of the subgroups specified herein, said radical independently is as specified above in the definition of the compounds of formulas (I) or in the more restricted definitions as specified hereinafter.

It should also be noted that the radical positions on any molecular moiety used in the definitions may be anywhere on such moiety as long as it is chemically stable. For instance pyridine includes 2-pyridine, 3-pyridine and 4-pyridine; pentyl includes 1-pentyl, 2-pentyl and 3-pentyl.

When any variable (e.g. halogen, $C_{1-6}$alkyl, aryl, Het, etc.) occurs more than one time in any moiety, each definition is independent.

Any limited definitions of the radicals specified herein are meant to be applicable to the group of compounds of formula (I) as well as to any subgroup defined or mentioned herein.

Lines drawn from substituents into ring systems indicate that the bond may be attached to any of the suitable ring atoms.

The term "compounds of formula (I)", or any similar terms such as "compounds of the invention" and the like, is meant to also comprise any N-oxide forms of the compounds of formula (I), which are compounds of formula (I) wherein one or several nitrogen atoms are oxidized to the N-oxide form.

The pharmaceutically acceptable addition salts that the compounds of the present invention are able to form can conveniently be prepared using the appropriate acids, such as, for example, inorganic acids such as hydrohalic acids, e.g. hydrochloric or hydrobromic acid, sulfuric, hemisulphuric, nitric, phosphoric and the like acids; or organic acids such as, for example, acetic, aspartic, dodecyl-sulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids. Conversely said acid addition salt forms can be converted by treatment with an appropriate base into the free base form.

The compounds of formula (I) containing acidic protons may be converted into their pharmaceutically acceptable metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethyl-amine, diethylamine, diethanolamine, dipropylamine, diisopropylamine, di-n-butylamine, pyrrolidine, piperidine, morpholine, trimethyl amine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The invention also comprises the hydrates and solvent addition forms which the compounds of formula (I) are able to form. Examples of such forms are e.g. hydrates, alcoholates and the like.

It will be appreciated that some of the compounds of formula (I) and the addition salts thereof may contain one or more centers of chirality and exist as stereochemically isomeric forms. Of special interest are those compounds of formula (I), which are stereochemically pure.

The term "stereochemically isomeric forms" as used hereinbefore defines all the possible stereoisomeric forms, which the compounds of formula (I) and the addition salts thereof may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their salts or solvates substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer. In particular, stereogenic centers may have the R- or S-configuration; substituents on bivalent cyclic (partially) saturated radicals may have either the cis- or trans-configuration.

Compounds having double bonds can have an E (entgegen) or Z (zusammen)-stereochemistry at said double bond. The terms cis, trans, R, S, E and Z are well known to a person skilled in the art.

Some of the compounds of formula (I) may also exist in their tautomeric form. Such forms although not explicitly indicated in the above formula are intended to be included within the scope of the present invention.

The present invention is also intended to include any isotopes of atoms present in the compounds of the invention. For example, isotopes of hydrogen include tritium and deuterium and isotopes of carbon include C-13 and C-14.

Whenever used hereinabove or hereinafter, the terms "compounds of formula (I)", "the present compounds", "the compounds of the present invention" or any equivalent terms, and similarly, the terms "subgroups of compounds of formula (I)", "subgroups of the present compounds", "subgroups of the compounds of the present invention" or any equivalent terms, are meant to include the compounds of general formula (I), or subgroups of the compounds of general formula (I), as well as their salts and stereoisomers.

Whenever mention is made hereinbefore or hereinafter that substituents can be selected each independently out of a list of definitions, such as for example for $R^8$ and $R^9$, any possible combinations are intended to be included, which are chemically possible or which lead to molecules of such chemical stability that they can be processed in standard pharmaceutical procedures.

Embodiment A of the present invention comprises those compounds of formula (I) or any of the subgroups of compounds of formula (I) wherein
$R^1$ is hydrogen.

Embodiment B of the present invention comprises those compounds of formula (I) or any of the subgroups of compounds of formula (I), such as those of embodiment A, wherein
(a) $R^2$, $R^3$, $R^7$ and $R^8$ independently are hydrogen; hydroxy; halo; $C_{1-6}$alkyl; $C_{3-7}$cyclo-alkyl; $C_{1-6}$ alkyloxy; carboxyl; $C_{1-6}$ alkyloxycarbonyl; cyano; nitro; amino; mono- or di($C_{1-6}$ alkyl)amino; polyhalo$C_{1-6}$ alkyl; polyhalo$C_{1-6}$ alkyloxy; —C(=O)$R^{10}$;
(b) $R^2$, $R^3$, $R^7$ and $R^8$ independently are hydrogen; hydroxy; halo; $C_{1-6}$alkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$ alkyl; —C(=O)$R^{10}$;
(c) $R^2$, $R^3$, $R^7$ and $R^8$ independently are hydrogen; hydroxy; halo; $C_{1-6}$alkyl; $C_{1-6}$alkyloxy; cyano; amino; mono- or di($C_{1-6}$alkyl)amino; polyhalo$C_{1-6}$ alkyl;
(d) $R^2$, $R^3$, $R^7$ and $R^8$ independently are hydrogen; halo; $C_{1-6}$alkyl; $C_{1-6}$alkyloxy; cyano;
(e) $R^2$, $R^3$, $R^7$ and $R^8$ independently are hydrogen; halo; $C_{1-6}$alkyl; cyano;
(f) $R^2$ and $R^3$ are hydrogen and $R^7$ and $R^8$ independently are hydrogen; halo; cyano.

Embodiment C of the present invention comprises those compounds of formula (I) or any of the subgroups of compounds of formula (I), such as those of embodiments A or B, wherein
(a) $R^4$ and $R^9$ independently are hydroxy; halo; $C_{1-6}$alkyloxy; carboxyl; $C_{1-6}$alkyloxy-carbonyl; formyl; cyano; amino; mono- or di($C_{1-6}$alkyl)amino; polyhalo$C_{1-6}$alkyl; —C(=O)$R^{10}$; Het; —Y-Het; $C_{1-12}$ alkyl optionally substituted with halo, cyano, amino, mono- and di($C_{1-6}$alkyl) amino, —C(=O)—$R^{10}$, Het; $C_{2-12}$ alkenyl optionally substituted with halo, cyano, amino, mono- and di($C_{1-6}$alkyl)amino, —C(=O)—$R^{10}$, Het; $C_{2-12}$alkynyl optionally substituted with halo, cyano, amino, mono- or di($C_{1-6}$ alkyl)amino, —C(=O)—$R^{10}$, Het;
(b) $R^4$ and $R^9$ independently are hydroxy; halo; $C_{1-6}$alkyloxy; carboxyl; $C_{1-6}$alkyloxy-carbonyl; formyl; cyano; amino; mono- or di($C_{1-6}$alkyl)amino; polyhalo$C_{1-6}$alkyl; —C(=O)$R^{10}$; Het; —Y-Het; $C_{1-12}$alkyl optionally substituted with halo, cyano, amino, mono- or di($C_{1-6}$alkyl) amino, —C(=O)—$R^{10}$, Het; $C_{2-12}$ alkenyl optionally substituted with halo, cyano, amino, mono- or di($C_{1-6}$ alkyl)amino, —C(=O)—$R^{10}$, Het; $C_{2-12}$alkynyl optionally substituted with halo, cyano, amino, mono- or di($C_{1-6}$ alkyl)amino, —C(=O)—$R^{10}$, Het; and wherein each Het in particular is independently selected from thienyl, furanyl, oxazolyl, thiazolyl, optionally substituted with halo, $C_{1-6}$alkyl, cyano, carboxyl, —C(=O)—$R^{10}$;
(c) $R^4$ and $R^9$ independently are hydroxy; halo; $C_{1-6}$alkyloxy; carboxyl; $C_{1-6}$alkyloxy-carbonyl; cyano; amino; mono- or di($C_{1-6}$alkyl)amino; —C(=O)$R^{10}$; Het. —Y-Het; $C_{1-6}$alkyl optionally substituted with cyano, —C(=O)—$R^{10}$, Het; $C_{2-6}$ alkenyl optionally substituted with cyano, —C(=O)—$R^{10}$, Het; $C_{2-6}$alkynyl optionally substituted with cyano, —C(=O)—$R^{10}$, Het; and wherein each Het in particular is independently selected from thienyl, furanyl, oxazolyl, thiazolyl, optionally substituted with halo, $C_{1-6}$alkyl, cyano, carboxyl, —C(=O)—$R^{10}$;
(d) $R^4$ and $R^9$ independently are halo; carboxyl; $C_{1-6}$alkyloxycarbonyl; cyano; —C(=O)—$R^{10}$; Het; —Y-Het; $C_{1-6}$alkyl optionally substituted with cyano, —C(=O)—$R^{10}$, Het; $C_{2-12}$alkenyl optionally substituted with cyano, —C(=O)—$R^{10}$, Het; and wherein each Het in particular is independently selected from thienyl, furanyl, oxazolyl, thiazolyl, optionally substituted with halo, $C_{1-6}$alkyl, cyano, carboxyl, —C(=O)—$R^{10}$;

(e) $R^4$ and $R^9$ independently are cyano; —C(=O)$R^{10}$; Het; $C_{1-6}$alkyl optionally substituted with cyano, —C(=O)—$R^{10}$, Het; $C_{2-6}$alkenyl optionally substituted with cyano, —C(=O)—$R^{10}$, Het; and wherein each Het in particular is independently thienyl or furanyl, each optionally substituted with cyano, —C(=O)—$R^{10}$;

(f) $R^4$ and $R^9$ independently are cyano; $C_{1-6}$alkyl substituted with cyano; $C_{2-6}$alkenyl substituted with cyano.

Embodiment D of the present invention comprises those compounds of formula (I) or any of the subgroups of compounds of formula (I), such as those of embodiments A, B or C, wherein (a) $R^5$ is $C_{3-7}$cycloalkyl; $C_{1-6}$alkyloxy; aryl; Het; $C_{1-6}$alkyl substituted with a radical selected from hydroxy, $C_{1-6}$alkyloxy, cyano, amino, mono- and di-$C_{1-6}$alkylamino, $C_{1-6}$alkylcarbonylamino, aryl, Het, dioxolanyl optionally substituted with one or two $C_{1-6}$alkyl radicals, tetrahydrofuranyl, pyrrolidinyl, piperidinyl, morpholinyl, piperazinyl, piperazinyl optionally substituted with $C_{1-6}$alkyl, $C_{1-6}$alkyloxycarbonyl, aryl$C_{1-6}$alkyloxycarbonyl, and $C_{3-7}$cycloalkyl;
$R^6$ is hydrogen or $C_{1-6}$alkyl; or
$R^5$ and $R^6$ taken together with the nitrogen atom to which they are substituted form pyrrolidinyl; piperidinyl; morpholinyl; piperazinyl optionally substituted with $C_{1-6}$alkyl;

(b) $R^5$ is $C_{3-7}$cycloalkyl; $C_{1-6}$alkyloxy; aryl; Het; $C_{1-6}$alkyl substituted with a radical selected from hydroxy, $C_{1-6}$alkyloxy, cyano, di-$C_{1-6}$alkylamino, $C_{1-6}$alkyl-carbonylamino, aryl, Het, dioxolanyl substituted with two $C_{1-6}$alkyl radicals, tetrahydrofuranyl, pyrrolidinyl, $C_{1-6}$alkyloxycarbonyl, and $C_{3-7}$cycloalkyl;
$R^6$ is hydrogen or $C_{1-6}$alkyl; or
$R^5$ and $R^6$ taken together with the nitrogen atom to which they are substituted form morpholinyl; piperazinyl substituted with $C_{1-6}$alkyl;

(c) $R^5$ is $C_{3-7}$cycloalkyl; $C_{1-6}$alkyloxy; $C_{1-6}$alkyl substituted with a radical selected from hydroxy, $C_{1-6}$ alkyloxy, cyano, $C_{1-6}$ alkylcarbonylamino, aryl, Het, $C_{1-6}$alkyloxycarbonyl;
$R^6$ is hydrogen;

(d) $R^5$ is $C_{1-6}$alkyl substituted with a radical selected from cyano, Het;

wherein in (a), (b), (c) or (d) aryl and Het are as in the definitions of the compounds of formula (I) or (I'), or subgroups of these compounds; or wherein in (a), (b), (c) or (d) aryl is phenyl optionally substituted with $C_{1-6}$alkyl, $C_{1-6}$alkyloxy, halo, aminosulfonyl, di$C_{1-6}$alkylamino; and/or Het is pyridyl, thienyl, furanyl each optionally substituted with $C_{1-6}$alkyl; or wherein in (a), (b), (c) or (d) Het preferably is pyridyl; or wherein in (a), (b), (c) or (d) $C_{3-7}$cycloalkyl is cyclopropyl.

Embodiment E of the present invention comprises those compounds of formula (I) or any of the subgroups of compounds of formula (I), such as those of embodiments A, B, C, or D, wherein each aryl independently may be as defined herein or in particular each aryl independently may be phenyl optionally substituted with $C_{1-6}$alkyl. amino, mono- or di$C_{1-6}$alkylamino, $C_{1-6}$alkyloxy, aminosulfonyl, Het, the latter more in particular being thiadiazolyl.

Embodiment F of the present invention comprises those compounds of formula (I) or any of the subgroups of compounds of formula (I), such as those of embodiments A, B, C, D or E, wherein each Het independently may be as defined herein or in particular each Het independently may be pyridyl, thienyl, thiazolyl, furanyl, each of which may be optionally substituted with $C_{1-6}$alkyl; or more in particular each Het independently may be pyridyl optionally substituted with $C_{1-6}$alkyl, thienyl, thiazolyl, furanyl optionally substituted with $C_{1-6}$alkyl.

Embodiment G of the present invention comprises those compounds of formula (I) or any of the subgroups of compounds of formula (I), such as those of embodiments A, B, C, D, E or F, wherein each $R^{16}$ independently is $C_{1-6}$alkyl, amino, mono- or di($C_{1-6}$alkyl)amino.

Embodiment H of the present invention comprises those compounds of formula (I) or any of the subgroups of compounds of formula (I), such as those of embodiments A, B, C, D, E, F and G, wherein X is —$NR^1$—, —O—, —S—, —S(=O)r-;

X is —$NR^1$—, —O—;

X is —$NR^1$—;

X is —NH—;

Embodiment I of the present invention comprises those compounds of formula (I) or any of the subgroups of compounds of formula (I), such as those of embodiments A, B, C, D, E, F, G and H, wherein each Y independently is —$NR^1$—, —O—, —S—, —S(=O)$_r$—; or each Y independently is —$NR^1$—.

Embodiment J of the present invention comprises those compounds of formula (I) or any of the subgroups of compounds of formula (I), such as those of embodiments A, B, C, D, E, F, G, H and I, wherein each r independently is 2.

Embodiment K of the present invention comprises those compounds of formula (I) or any of the subgroups of compounds of formula (I), such as those of embodiments A, B, C, D, E, F, G, H, I and J, wherein each Het independently is pyridyl, thienyl, furanyl, oxazolyl, isoxazolyl, imidazolyl, pyrazolyl, thiazolyl, thiadiazolyl, oxadiazolyl, quinolinyl, benzothienyl, benzofuranyl; which each may optionally be substituted with one or two substituents each independently selected from $C_{1-6}$alkyl, halo, hydroxy, cyano, $C_{1-6}$alkyloxy, $C_{2-12}$alkenyl substituted with halo, hydroxy or with cyano.

Embodiment L of the present invention comprises those compounds of formula (I) or any of the subgroups of compounds of formula (I), such as those of embodiments A, B, C, D, E, F, G, H, I, J and K, wherein each aryl independently is phenyl or phenyl substituted with one, two or three substituents each independently selected from those mentioned above or in particular from:

(a) halo, hydroxy, $C_{1-6}$alkyl, $C_{2-6}$alkenyl, $C_{2-6}$alkynyl, hydroxy$C_{1-6}$alkyl, amino-$C_{1-6}$alkyl, mono and di($C_{1-6}$ alkyl)amino$C_{1-6}$alkyl, $C_{1-6}$alkylcarbonyl, $C_{3-7}$cycloalkyl, $C_{1-6}$ alkyloxy, phenyl$C_{1-6}$alkyloxy, $C_{1-6}$alkyloxycarbonyl, aminosulfonyl, cyano, nitro, polyhalo$C_{1-6}$ alkyl, polyhalo$C_{1-6}$alkyloxy, aminocarbonyl, phenyl, Het, and —Y-Het; or from (b) halo, hydroxy, $C_{1-6}$alkyl, hydroxy$C_{1-6}$alkyl, amino$C_{1-6}$ alkyl, mono and di($C_{1-6}$ alkyl)-amino $C_{1-6}$ alkyl, $C_{1-6}$ alkyloxy, phenyl$C_{1-6}$ alkyloxy, $C_{1-6}$ alkyloxycarbonyl, cyano, polyhalo$C_{1-6}$ alkyl, aminocarbonyl.

One embodiment of the present invention concerns compounds of formula

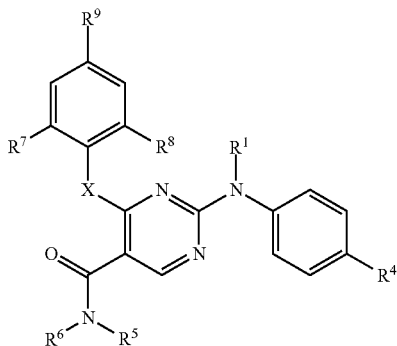

(I')

the pharmaceutically acceptable addition salts or stereochemically isomeric forms thereof, wherein X, $R^1$, $R^4$, $R^5$, $R^6$, $R^7$, $R^8$ and $R^9$ are as defined above.

In a particular embodiment, $R^9$ in the compounds of formula (I) or (I'), or any subgroup thereof, is —$CH_2$—$CH_2$—CN, —CH=CH—CN, or —C≡C—CN. Of particular interest are those compounds wherein $R^9$ is the (E)-isomer of —CH=CH—CN.

Another embodiment relates to those compounds of formula (I) or (I'), or any subgroup thereof, wherein one or more of the following restrictions apply:
(i) each $R^1$ independently is hydrogen, aryl, formyl, $C_{1-6}$alkylcarbonyl, $C_{1-6}$alkyl, $C_{1-6}$alkyloxycarbonyl;
(ii) $R^4$ is hydroxy, halo, $C_{1-6}$alkyl, carboxyl, cyano, —C(=O)$R^{10}$, nitro, amino, mono- or di($C_{1-6}$ alkyl)amino, polyhalomethyl;
(iii) X is —$NR^1$—, —O—, —S—, —S(=O)$_r$—;
(iv) $R^7$ is H, $C_{1-6}$alkyl, halo;
(v) $R^8$ is H, $C_{1-6}$alkyl, halo;
(vi) $R^5$ is $C_{3-7}$cycloalkyl; $C_{1-6}$alkyloxy; aryl; Het; $C_{1-6}$alkyl substituted with a radical selected from hydroxy, $C_{1-6}$alkyloxy, cyano, di-$C_{1-6}$alkylamino, $C_{1-6}$alkylcarbonylamino, aryl, Het, dioxolanyl substituted with two $C_{1-6}$alkyl radicals, tetrahydrofuranyl, pyrrolidinyl, $C_{1-6}$alkyloxycarbonyl, and $C_{3-7}$cycloalkyl;
$R^6$ is hydrogen or $C_{1-6}$alkyl; or
$R^5$ and $R^6$ taken together with the nitrogen atom to which they are substituted form morpholinyl; piperazinyl substituted with $C_{1-6}$alkyl;
(vii) $R^6$ is hydrogen or $C_{1-6}$alkyl; or in particular, $R^6$ is hydrogen;
(viii) each aryl is phenyl or phenyl substituted with one, two, three, four or five substituents each independently selected from halo, hydroxy, mercapto, $C_{1-6}$alkyl, hydroxy$C_{1-6}$alkyl, amino$C_{1-6}$ alkyl, mono and di($C_{1-6}$ alkyl)amino$C_{1-6}$alkyl, $C_{1-6}$alkylcarbonyl, $C_{3-7}$ cycloalkyl, $C_{1-6}$ alkyloxy, $C_{1-6}$ alkyloxycarbonyl, $C_{1-6}$ alkyl-thio, cyano, nitro, polyhalo$C_{1-6}$ alkyl, polyhalo$C_{1-6}$ alkyloxy, aminocarbonyl.

Another embodiment relates to those compounds of formula (I) or (I'), or any subgroup thereof, wherein one or more of the following restrictions apply:
(i) $R^9$ is —$CH_2$—$CH_2$—CN or —CH=CH—CN; or in particular wherein $R^9$ is —CH=CH—CN;
(ii) $R^1$ is hydrogen, formyl, $C_{1-6}$ alkylcarbonyl, $C_{1-6}$ alkyl, $C_{1-6}$ alkyloxycarbonyl;
(ii-a) $R^1$ is hydrogen, $C_{1-6}$alkyl;
(ii-b) $R^1$ is hydrogen, methyl;
(ii-c) $R^1$ is hydrogen;

(iii) $R^4$ is cyano, aminocarbonyl; or wherein (iii-a) $R^2$ is cyano.
(iv) X is —$NR^1$—, —O—;
(iv-a) X is —$NR^1$—,
(iv-b) X is —NH—, —N($C_{1-4}$alkyl)-, —O—;
(iv-c) X is —NH—;
(v) $R^7$ is H, $C_{1-6}$alkyl, halo;
(v-a) $R^7$ is H, $C_{1-4}$alkyl, halo;
(v-b) $R^7$ is $C_{1-4}$ alkyl.
(vi) $R^8$ is H, $C_{1-6}$alkyl, halo;
(vi-a) $R^8$ is H, $C_{1-4}$alkyl, halo;
(vi-b) $R^8$ is $C_{1-4}$ alkyl.
(vii) $R^5$ is $C_{3-7}$cycloalkyl; $C_{1-6}$alkyloxy; aryl; Het; $C_{1-6}$alkyl substituted with a radical selected from hydroxy, $C_{1-6}$alkyloxy, cyano, di$C_{1-6}$ alkylamino, $C_{1-6}$ alkylcarbonylamino, aryl, Het, dioxolanyl substituted with two $C_{1-6}$alkyl radicals, tetrahydrofuranyl, pyrrolidinyl, $C_{1-6}$alkyloxycarbonyl, and $C_{3-7}$cycloalkyl;
$R^6$ is hydrogen or $C_{1-6}$alkyl; or
$R^5$ and $R^6$ taken together with the nitrogen atom to which they are substituted form morpholinyl; piperazinyl substituted with $C_{1-6}$alkyl;
(viii) $R^6$ is hydrogen or $C_{1-6}$alkyl; or in particular, $R^6$ is hydrogen.

Still other subgroups of the compounds of formula (I) or (I') are those compounds of formula (I) or (I'), or any subgroup thereof, wherein
(a) $R^{10}$ is hydrogen, $C_{1-4}$alkyl; or wherein (b) $R^{10}$ is hydrogen or $C_{1-2}$alkyl.

Other subgroups of the compounds of formula (I) are those compounds of formula (I) or (I'), or any subgroup of those compounds, wherein
(a) aryl is phenyl or phenyl substituted with one, two or three substituents each independently selected from halo, hydroxy, mercapto, $C_{1-6}$alkyl, hydroxy$C_{1-6}$alkyl, amino$C_{1-6}$alkyl, mono and di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, cyano, nitro, polyhalo$C_{1-6}$alkyl, polyhalo$C_{1-6}$alkyloxy, aminocarbonyl.
(b) aryl is phenyl or phenyl substituted with one, two or three substituents each independently selected from halo, hydroxy, mercapto, $C_{1-6}$alkyl, hydroxy$C_{1-6}$alkyl, amino$C_{1-6}$alkyl, mono and di($C_{1-6}$alkyl)amino$C_{1-6}$alkyl, $C_{1-6}$alkylcarbonyl, $C_{1-6}$ alkyloxy, $C_{1-6}$alkyloxycarbonyl, $C_{1-6}$alkylthio, cyano, nitro, trifluoromethyl, trifluoromethoxy, aminocarbonyl.
(c) aryl is phenyl or phenyl substituted with one, two or three substituents each independently selected from halo, hydroxy, $C_{1-6}$alkyl, hydroxy$C_{1-6}$alkyl, amino-$C_{1-6}$alkyl, mono and di($C_{1-6}$alkyl)amino $C_{1-6}$alkyl, $C_{1-6}$alkylcarbonyl, $C_{1-6}$alkyloxy, $C_{1-6}$alkyloxycarbonyl, cyano, nitro, trifluoromethyl.
(d) aryl is phenyl or phenyl substituted with one, two or three substituents each independently selected from halo, hydroxy, $C_{1-6}$alkyl, $C_{1-6}$alkyloxy, cyano, nitro, trifluoromethyl.

Of particular interest are the compounds nos. 9, 10, 12, 14, 15, 19, 21, 23, 33, 37, 45, 46, 47, 49, 53, 54, and in particular compounds nos. 15 and 46, listed in the Tables of the experimental part.

The compounds of formula (I) can be prepared by reacting a carboxylic acid or an active form thereof (II) with an amine (III), in an amide bond forming reaction.

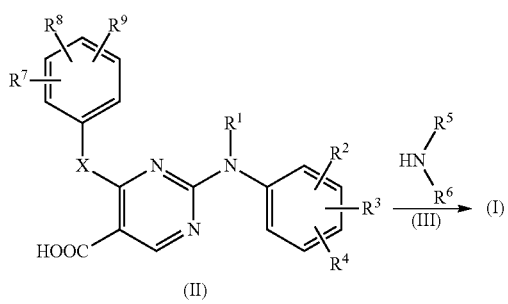

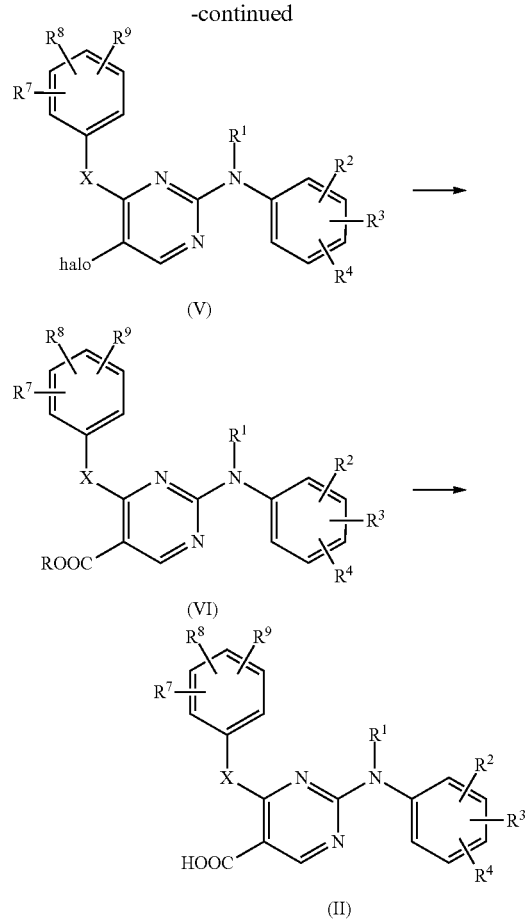

The amide bond forming reaction may be performed by reacting the starting material (II) in the presence of a coupling agent with an amine (III) or by converting the carboxyl functionality in (II) into an active form such as an active ester or a carboxylic acid halide, in particular an acid chloride or bromide, azide, mixed carbonic-carboxylic acid anhydride (e.g. by reaction with isobutyl chloroformate), or an active ester (e.g. a p-nitrophenyl ester, pentachlorophenylester, N-hydroxysuccinic imido ester). The amine (III) may also be reacted with a carboxylic acid lower alkyl ester, derivative of (III), in particular a methyl or ethyl ester. Examples of coupling agents include the carbodiimides (dicyclohexylcarbodiimide, diisopropylcarbodiimide, or water-soluble carbodiimide such as N-ethyl-N'-[(3-dimethylamino)propyl]carbodiimide) or carbonyldiimidazoles. Addition of a suitable catalysts may be recommended to enhance the reaction rate, e.g. in the carbodiimide method by adding 1-hydroxybenzotriazole or 4-DMAP.

The amide bond forming reactions preferably are conducted in reaction-inert solvents, such as halogenated hydrocarbons, e.g. dichloromethane, chloroform, dipolar aprotic solvents such as acetonitrile, dimethylformamide, dimethylacetamide, ethers such as tetrahydrofuran. In many instances the coupling reactions take place in the presence of a suitable base such as a tertiary amine, e.g. triethylamine, diisopropylethylamine (DIPEA), N-methylmorpholine, N-methylpyrrolidine, or 4-DMAP.

The intermediates (II) can be prepared by first halogenating a starting material of formula (IV), which can be prepared as described in WO 03/016306. Other leaving groups can be introduced by replacing the halo group using suitable reagents. The thus obtained intermediates (V) are converted to the corresponding intermediates (VI), which have a group —COOR in the 5-position of the pyrimidine moiety. R in this group may be a $C_{1-6}$alkyl radical, in particular a $C_{1-2}$alkyl radical. In a next step, the intermediates (VI) are reacted with pressurized CO gas in the presence of a $C_{1-6}$alkanol, in particular methanol or ethanol, and a suitable catalyst, e.g. dichlorobis(triphenyl-phosphine)-palladium(II). The intermediates (VI) in turn are converted into the corresponding acids (II) by art-known ester to acid conversion reaction under basic or acidic conditions.

The intermediates (IV) in the above reaction scheme have been described in WO 99/50250 or can be prepared following synthesis procedures described in this reference.

The intermediates of formula (II) can also be prepared by reacting an intermediate of formula (VII), wherein W represents a suitable leaving group, as specified above, and A represents a protected carboxyl group such as a group

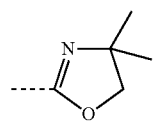

with an intermediate of formula (VIII).

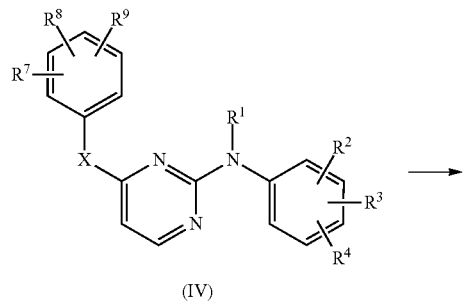

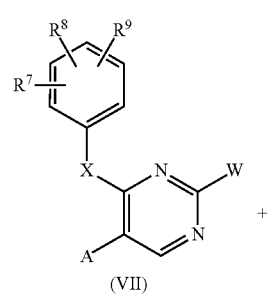

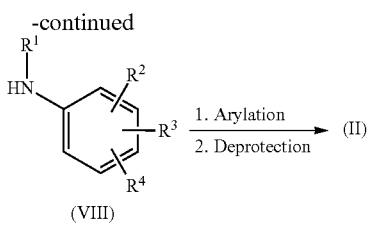

The reaction of (VII) with (VIII) typically is conducted in the presence of a suitable solvent. Suitable solvents are, for example, alcohols, such as for example ethanol, 2-propanol; dipolar aprotic solvents such as acetonitrile, N,N-dimethylformamide, N,N-dimethylacetamide, 1-methyl-2-pyrrolidinone; ethers such as tetrahydrofuran, 1,4-dioxane, or propylene glycol monomethylether. The conditions for the removal of the carboxyl-protecting group depend on the nature of the group that is used. For example for the dihydrooxazole group mentioned above, removal will be by treatment with an acid.

Intermediates of formula (VI) wherein X is O, said intermediates being represented by formula (VI-a), can be prepared by reacting an intermediate of formula (IX) with an intermediate of formula (X) in a Mitsonobu type of reaction, i.e. by reacting the starting materials with an azodicarboxylate/triphenyl phosphine reagent, for example diisopropylazodicarboxylate (DIAD), in a solvent such as methanol or THF.

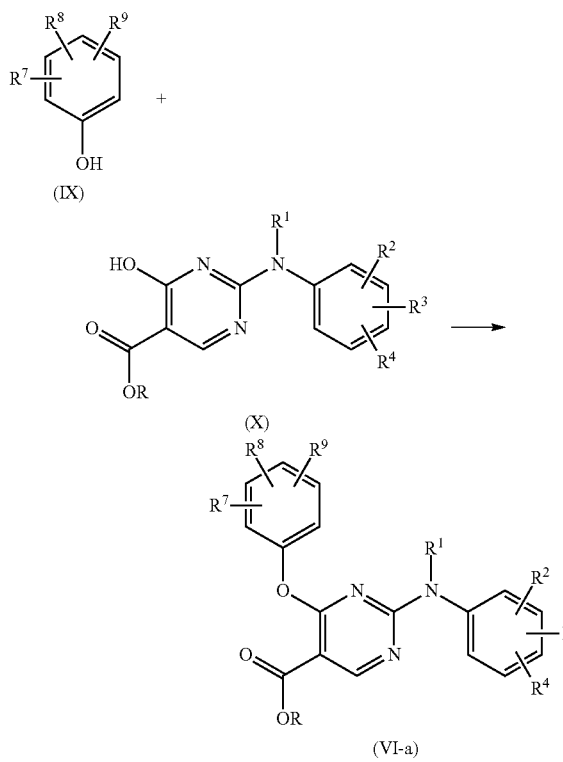

The compounds of formula (I) may be converted to the corresponding N-oxide forms following art-known procedures for converting a tertiary nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboper-oxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The compounds of formula (I) may further be converted into each other using art-known functional group transformation reactions. Compounds of formula (I) wherein $R^2$ or $R^3$ is hydrogen, can be converted into a compounds of formula (I) wherein one or more of $R^2$, $R^3$, $R^7$ or $R^8$ represents halo, by reaction with a suitable halo-introducing agent, e.g. N-chlorosuccinimide or N-bromosuccinimide, in the presence of a suitable solvent, e.g. acetic acid. Compounds of formula (I) wherein $R^1$ represents $C_{1-6}$alkyloxycarbonyl, can be converted into a compound of formula (I) wherein $R^1$ represents hydrogen, by reaction with a suitable base, such as for example sodium hydroxide or methoxide. Where $R^1$ is t.butyloxycarbonyl, the corresponding compounds wherein $R^1$ is hydrogen are prepared by treatment with trifluoroacetic acid.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures.

Intermediates of formula (VII) can be prepared by reacting an intermediate of formula (XI), wherein W is as specified above, with an intermediate of formula (XII), in the presence of a suitable solvent, e.g. tetrahydrofuran, and optionally in the presence of a suitable base, e.g. $Na_2CO_3$. The group "A" in the following reaction scheme is as defined above but may also represent a carboxylic ester (—COOR wherein R is as described above), which is converted into a protected carboxyl group, which can be as described above.

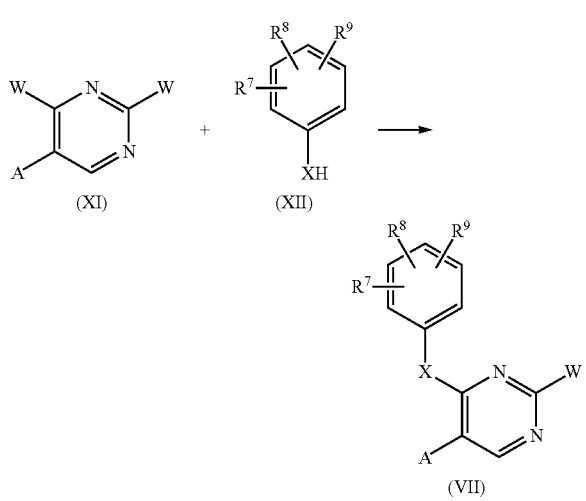

The intermediates (X) can be prepared as follows:

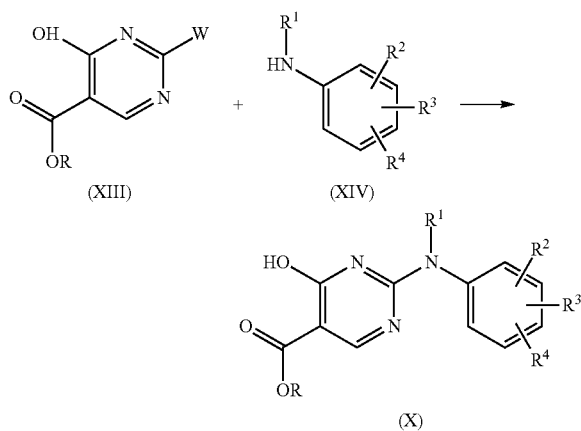

W and R in the above scheme are as specified above.

The compounds of formula (I) have antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever-decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against (multi) drug resistant HIV strains, in particular (multi) drug resistant HIV-1 strains, more in particular the present compounds show activity against HIV strains, especially HIV-1 strains that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and known to the person skilled in the art, in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I), the pharmaceutically acceptable addition salts and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In further aspect of this invention, there is provided a method of treating warm-blooded animals, including humans, suffering from conditions associated with viral infection, in particular HIV infection, said method comprising the administration to said warm-blooded animals, including humans, an anti-virally effective amount of a compound of formula (I) as specified herein. Furthermore there is provided a method of preventing the development of conditions associated with viral infection, in particular HIV infection, in warm-blooded animals, including humans, said method comprising the administration to said warm-blooded animals, including humans, an anti-virally effective amount of a compound of formula (I) as specified herein.

The present invention also provides compositions for treating viral infections comprising a therapeutically effective amount of a compound of formula (I) and a pharmaceutically acceptable carrier or diluent.

The compounds of the present invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclo-dextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy-$C_{1-6}$alkyl, particularly carboxymethyl or carboxy-ethyl; $C_{1-6}$alkyl carbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclo-dextrin hydroxy groups are etherified with different groups such as, for example, hydroxy-propyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in case the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermo-dynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions, which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:

a) mixing a compound of formula (I) and an appropriate water-soluble polymer,
b) optionally blending additives with the thus obtained mixture,
c) heating and compounding the thus obtained blend until one obtains a homogenous melt,
d) forcing the thus obtained melt through one or more nozzles; and
e) cooling the melt until it solidifies.

The terms "melt" and "melting" are not only meant to refer to the transition from a solid state to a liquid state, but also to refer to the transition to a glassy state or a rubbery state, in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved. The solid dispersion product may be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkyl-celluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gum arabic, guar gum and xanthan gum, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water-soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl-$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxy-methyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a M.S. value of about 0.125 to 10, e.g. about 0.3 to 3. Another type of substituted cyclodextrins that can be used are the sulfobutylcyclodextrins.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound. Suitable surface modifiers can preferably be selected from known organic and inorganic pharmaceutical excipients. Such excipients include various polymers, low molecular weight oligomers, natural products and surfactants. Preferred surface modifiers include non-ionic and anionic surfactants.

Yet another way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration. These beads comprise a central, rounded or spherical core, a coating film of a hydrophilic polymer and a compound of formula (I) and optionally a seal-coating layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The compounds of formula (I) can be used alone or in combination with other therapeutic agents, such as antivirals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126,443), AVX 754 ((−)-dOTC), fozivudine tidoxil (FZT), phosphazide, HDP-990003, KP-1461, MIV-210, racivir (PSI-5004), UC-781 and the like; non-nucleoside reverse transcriptase inhibitors (NNRTIs) such as delavirdine (DLV), efavirenz (EFV), nevirapine (NVP), dapivirine (TMC120), etravirine (TMC125), rilpivirine (TMC278), DPC-082, (+)-Calanolide A, BILR-355, and the like; nucleotide reverse transcriptase inhibitors (NtRTIs), e.g. tenofovir ((R)-PMPA) and tenofovir disoproxil fumarate (TDF), and the like; nucleotide-competing reverse transcriptase inhibitors (NcRTIs), such as the compounds described in WO2004/046143; inhibitors of trans-activating proteins, such as TAT-inhibitors, e.g. RO-5-3335, BI-201, and the like; REV inhibitors; protease inhibitors e.g. ritonavir (RTV), saquinavir (SQV), lopinavir (ABT-378 or LPV), indinavir (IDV), amprenavir (VX-478), TMC126, nelfinavir (AG-1343), atazanavir (BMS 232,632), darunavir (TMC114), fosamprenavir (GW433908 or VX-175), brecanavir (GW-640385, VX-385), P-1946, PL-337, PL-100, tipranavir (PNU-140690), AG-1859, AG-1776, Ro-0334649 and the like; entry inhibitors which comprise fusion inhibitors (e.g. enfuvirtide (T-20)), attachment inhibitors and co-receptor inhibitors, the latter comprise the CCR5 antagonists (e.g. ancriviroc, CCR5mAb004, maraviroc (UK-427, 857), PRO-140, TAK-220, TAK-652, vicriviroc (SCH-D, SCH-417,690)) and CXR4 antagonists (e.g. AMD-070, KRH-27315), examples of entry inhibitors are PRO-542, TNX-355, BMS-488,043, BlockAide/CR™, FP 21399, hNM01, nonakine, VGV-1; a maturation inhibitor for example is PA-457; inhibitors of the viral integrase e.g. MK-0518, JTK-303 (GS-9137), BMS-538,158; ribozymes; immunomodulators; monoclonal antibodies; gene therapy; vaccines; siRNAs; antisense RNAs; microbicides; Zinc-finger inhibitors.

The compounds of the present invention may also be administered in combination with immunomodulators (e.g., bropirimine, anti-human alpha interferon antibody, IL-2, methionine enkephalin, interferon alpha, and naltrexone) with antibiotics (e.g. pentamidine isothiorate) cytokines (e.g. Th2), modulators of cytokines, chemokines or modulators of chemokines, chemokine receptors (e.g. CCR5, CXCR4), modulators chemokine receptors, or hormones (e.g. growth hormone) to ameliorate, combat, or eliminate HIV infection and its symptoms. Such combination therapy in different formulations, may be administered simultaneously, sequentially or independently of each other. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. It is known that several isoenzymes exist of cytochrome P450, one of which is cytochrome P450 3A4. Ritonavir is an example of a modulator of metabolization via cytochrome P450. Such combination therapy in different formulations, may be administered simultaneously, sequentially or independently of each other. Alternatively, such combination may be administered as a single formulation, whereby the active ingredients are released from the formulation simultaneously or separately. Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

Although the present invention focuses on the use of the present compounds for preventing or treating HIV infections, the present compounds may also be used as inhibitory agents for other viruses which depend on similar reverse transcriptases for obligatory events in their life cycle.

The following examples are intended to illustrate the present invention and not to limit its scope thereto.

EXAMPLES

Example 1

Preparation of Intermediate 2

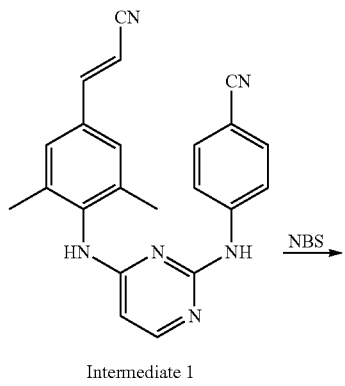

Intermediate 1

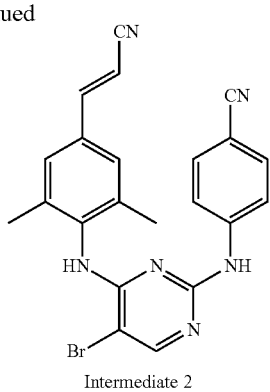

Intermediate 2

N-bromosuccinimide (0.0393 mol) was added portion wise at room temperature to Intermediate 1 (0.0327 mol), the preparation of which is described in WO-03/016306, in CH₃CN (100 ml). The mixture was stirred at room temperature for 4 hours. The precipitate was filtered off, washed with CH₃CN and dried yielding 10.08 g of the desired end product. The filtrate was evaporated and purified by column chromatography (eluent: CH₂Cl₂ 100; 35-70 μm). The pure fractions were collected, the solvent was evaporated and the residue was crystallized from CH₃CN. Yield: 2.4 g of Intermediate 2. The two fractions were collected. Total yield: 12.48 g of intermediate 2 (86%, melting point: >250° C.).

Example 2

Preparation of Intermediate 3

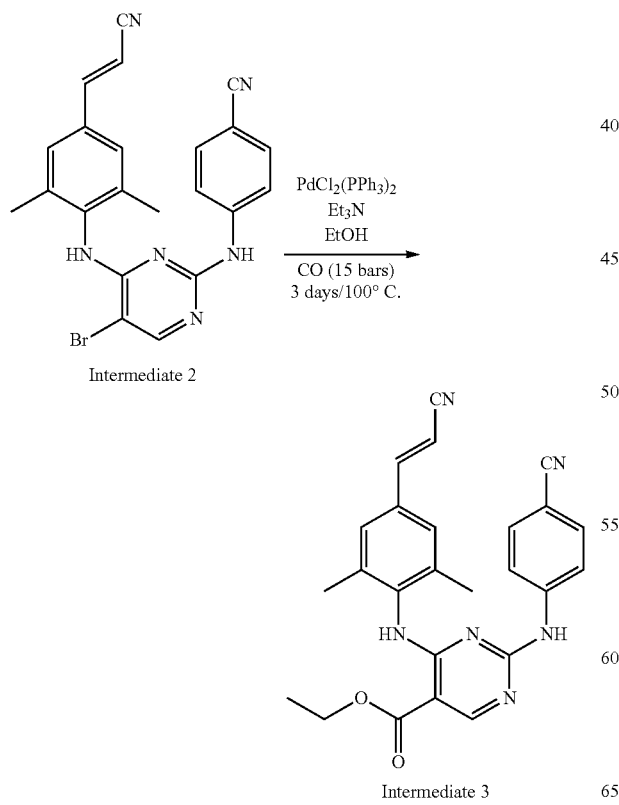

Intermediate 3

A mixture of intermediate 2 (0.0247 mol), dichlorobis(triphenylphosphine)-palladium(II) (0.00494 mol) and triethylamine (0.107 mol) in ethanol (100 ml) were stirred at 100° C. for 72 hours under 15 bars pressure of carbon monoxide. The mixture was poured in water and the precipitate was filtered off, yielding 6 g of intermediate 3. The filtrate was extracted with CH₂Cl₂. The organic layer was dried over magnesium sulfate, filtered and the solvent was evaporated. The residue was purified by column chromatography over silica gel (eluent: CH₂Cl₂/MeOH 99.5/0.5; 15-40 μm)). The pure fractions were collected and the solvent evaporated. Yield: 1.9 g. The two fractions were combined, yielding 7.9 g of intermediate 3 (73%, melting point: >250° C.).

Example 3

Preparation of Intermediate 4

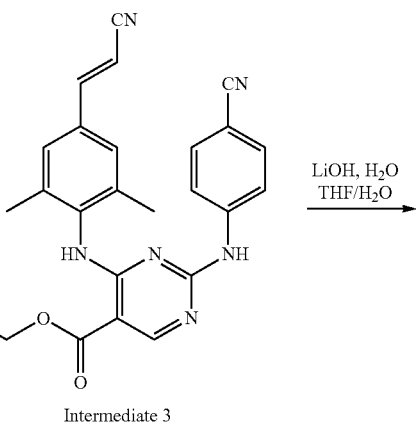

Intermediate 3

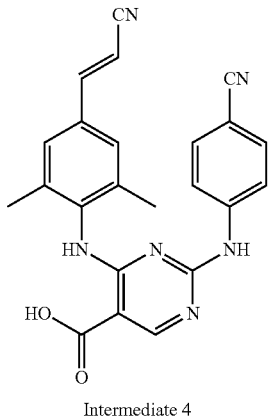 [SMILES: Cc1cc(/C=C/C#N)cc(C)c1Oc1nc(Nc2ccc(C#N)cc2)ncc1C(=O)O]

Intermediate 4

A mixture of intermediate 3 (0.00456 mol), lithium hydroxide, monohydrate (0.0137 mol) in THF (20 ml) and water (7 ml) were stirred at 50° C. overnight. The THF was evaporated. The residue was diluted in water and HCl 3N was added until pH 2-3. The precipitate was filtered off, washed with water and dried. Yield: 1.78 g of intermediate 4 (95%, melting point: >250° C.).

Example 4

Amide Synthesis

Method A:

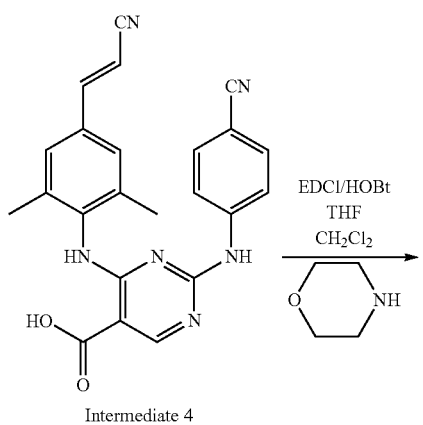

Intermediate 4

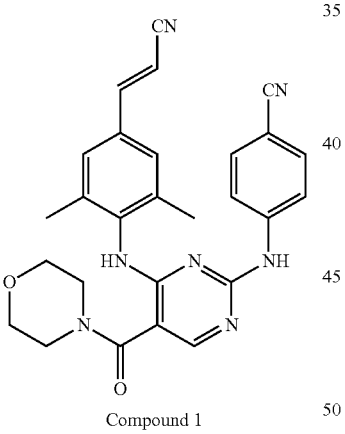

Compound 1

1-hydroxybenzotriazole (0.000183 mmol, 1.5 eq) was added to a mixture of intermediate 4 (0.00122 mmol, 1.5 eq) in THF (3 ml). Dichloromethane (3 ml) and 1-(3-dimethylaminopropyl)-3-ethylcarbodiimide hydrochloride (0.00183 mmol, 1.5 eq) were added successively to the mixture. To this solution, morpholine (0.00183 mmol, 1.5 eq) was added. The mixture was stirred at room temperature for 24 h then poured in water and $K_2CO_3$ 10% and extracted with a 90/10 mixture of $CH_2Cl_2$ and methanol. The organic layer was washed with a solution of brine, dried over magnesium sulfate, filtered and the solvent evaporated. The residue was purified by column chromatography over silica gel (eluent: $CH_2Cl_2$/MeOH 99/1; $SiO_2$ 70-200). Yield: 0.055 g of compound 1 (94%, melting point: >250° C.).

Example 5
Method B

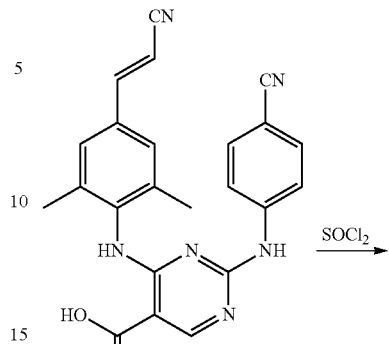

Intermediate 4

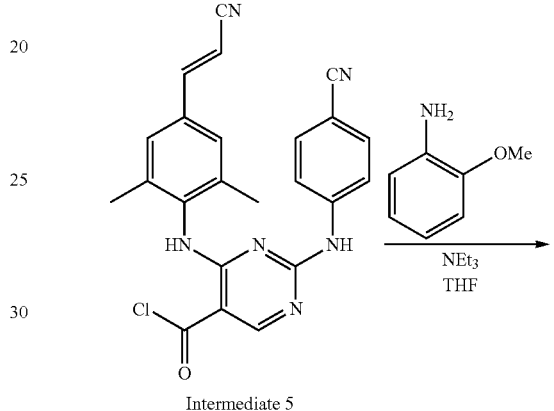

Intermediate 5

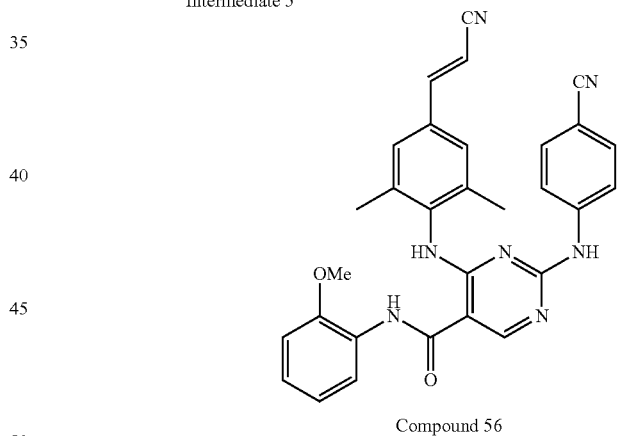

Compound 56

Thionyl chloride (7 ml) was added to intermediate 4 (0.000734 mmol). The mixture was heated to reflux 1.5 hour, then evaporated to dryness. The residue was purified by trituration in diethyl ether. Yield: 0.3 g of intermediate 5 (95%).

A mixture of intermediate 5 (0.000233 mol), 2-aminoanisole (0.00035 mol, 1.5 eq) and triethylamine (0.00035 mol, 1.5 eq) in THF (5 ml) and $CH_2Cl_2$ (5 ml) was stirred at room temperature for 24 hours, then poured in water and $K_2CO_3$ 10% and extracted with AcOEt. The organic layer was washed with a solution of brine, dried over magnesium sulfate, filtered and the solvent evaporated. The residue was purified by column chromatography (eluent: $CH_2Cl_2$ 100% to $CH_2Cl_2$/MeOH 98/2; Kromasil 3.5 μm 150*30). Yield: 0.052 g of compound 56 (53%, melting point: >250° C.).).

The following tables list compounds which were or can be prepared according to the procedures described in the above examples.

TABLE 1

[Structure: Pyrimidine core with (E)-cyanovinyl-dimethylphenyl-NH at 4-position, 4-cyanophenyl-NH at 2-position, and R-C(=O)- at 5-position]

| Compound No. | Method | R | Phys. Data and stereochemistry |
|---|---|---|---|
| 1 | A | morpholin-4-yl | (E) Yield 94% >250° C. |
| 2 | A | piperidin-1-yl | (E) Yield 69% >250° C. |
| 3 | A | pyridin-2-yl-NH- | (E) Yield 51% >250° C. |
| 4 | A | (CH₃)₂N-CH₂CH₂-N(CH₃)- | (E) Yield 60% 230° C. |
| 5 | A | phenyl-N(CH₃)- | (E) Yield 38% 238° C. |
| 6 | A | 4-methylpiperazin-1-yl | (E/Z:93/7) Yield 48% 221° C. |
| 7 | A | HO-CH₂CH₂-N(CH₃)- | (E) Yield 50% 175° C. |
| 8 | A | NC-CH₂CH₂-N(CH₃)- | (E) Yield 43% 218° C. |
| 9 | A | CH₃O-CH₂CH₂CH₂-NH- | (E) 62% 214° C. |
| 10 | A | (2,2-dimethyl-1,3-dioxolan-4-yl)methyl-NH- | (E) Yield 78% 246° C. |
| 11 | A | ethoxycarbonylmethyl-N(CH₃)- | (E) Yield 60% 227° C. |
| 12 | A | (tetrahydrofuran-2-yl)methyl-NH- | (E) Yield 67% 238° C. |
| 13 | A | CH₃O-N(CH₃)- | (E) Yield 62% >250° C. |
| 14 | A | ethoxycarbonyl-CH₂CH₂-NH- | (E) Yield 32% 246° C. |
| 15 | A | (pyridin-4-yl)methyl-NH- | (E) Yield 63% >250° C. |
| 16 | A | (3-chlorophenyl)-NH- | (E/Z:96/4) Yield 19% >250° C. |
| 17 | A | (4-chlorophenyl)-NH- | (E) Yield 25% >250° C. |
| 18 | A | benzyl-N(CH₃)- | (E/Z:96/4) Yield 27% 226° C. |
| 19 | A | (furan-2-yl)methyl-NH- | (E) Yield 45% >250° C. |
| 20 | A | (thiophen-2-yl)methyl-NH- | (E) Yield 44% >250° C. |

TABLE 1-continued

[Structure: pyrimidine with 2-((4-cyanophenyl)amino) and 4-((4-(2-cyanovinyl)-2,6-dimethylphenyl)amino) substituents, and a 5-C(=O)R group]

| Compound No. | Method | R | Phys. Data and stereochemistry |
|---|---|---|---|
| 21 | A | NC-CH₂-NH- | (E/Z:98/2) Yield 39% >250° C. |
| 22 | B | (CH₃)₂N-CH₂CH₂-NH- | (E) Yield 68% 226° C. |
| 23 | B | MeO-NH- | (E) Yield 28% >250° C. |
| 24 | B | 5-methylfuran-2-ylmethyl-NH- | (E) Yield 26% 226° C. |
| 25 | A | 3-chlorobenzyl-NH- | (E) Yield 37% >250° C. |
| 26 | A | 4-fluorobenzyl-NH- | (E) Yield 58% >250° C. |
| 27 | A | 2-methoxybenzyl-NH- | (E) Yield 31% >250° C. |
| 28 | A | 3-methylbenzyl-NH- | (E) Yield 59% >250° C. |
| 29 | A | 3-bromobenzyl-NH- | (E) Yield 39% >250° C. |
| 30 | A | 4-(dimethylamino)benzyl-NH- | (E) Yield 18% >250° C. |
| 31 | A | phenethyl-NH- | (E) Yield 53% >250° C. |
| 32 | A | 3-fluorophenethyl-NH- | (E) Yield 50% >250° C. |
| 33 | A | CH₃C(=O)NH-CH₂CH₂-NH- | (E) Yield 45% >250° C. |
| 34 | A | benzyl-O-C(=O)-CH₂-NH- | (E) Yield 9% >250° C. |
| 35 | A | 4-methylpyridin-2-yl-NH- | (E) Yield 15% >250° C. |
| 36 | A | 4-bromobenzyl-NH- | (E) Yield 14% >250° C. |
| 37 | A | cyclopropyl-NH- | (E) Yield 65% >250° C. |
| 38 | A | pyrrolidin-1-yl-propyl-NH- | (E) Yield 43% >250° C. |
| 39 | A | 4-bromophenethyl-NH- | (E) Yield 36% >250° C. |

TABLE 1-continued

Structure for compounds 40-49:
A pyrimidine core with a 4-NH-(2,6-dimethyl-4-(2-cyanovinyl)phenyl) group, a 2-NH-(4-cyanophenyl) group, and a 5-C(=O)-R substituent.

| Compound No. | Method | R | Phys. Data and stereochemistry |
|---|---|---|---|
| 40 | A | N-methyl-N-benzyl-propylamino (BnN(Me)CH₂CH₂CH₂NH–) | (E) Yield 43% 199° C. |
| 41 | A | cyclopropylmethylamino | (E) Yield 56% >250° C. |
| 42 | A | cyclohexylmethylamino | (E) Yield 21% >250° C. |
| 43 | A | 3-(dimethylamino)propylamino (Me₂N(CH₂)₃NH–) | (E) Yield 56% 226° C. |
| 44 | A | 2-(pyridin-2-yl)ethylamino | (E) Yield 66% 245° C. |
| 45 | A | ethyl 4-aminobutanoate (EtO₂C(CH₂)₃NH–) | (E) Yield 66% 222° C. |
| 46 | A | 2-cyanoethylamino (NC-CH₂CH₂-NH–) | (E) Yield 40% >250° C. |
| 47 | A | 2-(4-sulfamoylphenyl)ethylamino | (E) Yield 85% 221° C. |
| 48 | A | 2-(thiophen-2-yl)ethylamino | (E) Yield 77% 250° C. |
| 49 | A | 3-hydroxypropylamino (HO(CH₂)₃NH–) | (E) Yield 57% >250° C. |

TABLE 1-continued

Structure for compounds 50-57: same core as above.

| Compound No. | Method | R | Phys. Data and stereochemistry |
|---|---|---|---|
| 50 | A | 4-(1,2,3-thiadiazol-4-yl)phenylamino | (E) Yield 11% >250° C. |
| 51 | A | 2-(pyrrolidin-1-yl)ethylamino | (E) Yield 49% 225° C. |
| 52 | A | 4-(1,2,3-thiadiazol-4-yl)benzylamino | (E) Yield 32% 260° C. |
| 53 | A | 2-hydroxyethylamino (HOCH₂CH₂NH–) | (E/Z 93/7) mp >250° C. |
| 54 | A | 2-methoxyethylamino (MeOCH₂CH₂NH–) | (E/Z 94/6) mp >250° C. |
| 55 | A | N-ethyl-N-(2-hydroxyethyl)amino | (E/Z 94/6) mp >222° C. |
| 56 | B | 2-methoxyphenylamino | E mp >250° C. |
| 57 | A | thiazol-2-ylamino | E |

Example 6

Preparation of Intermediate 11

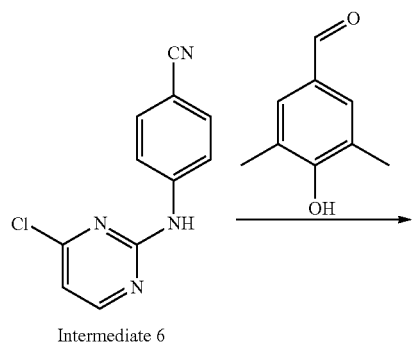

Intermediate 6

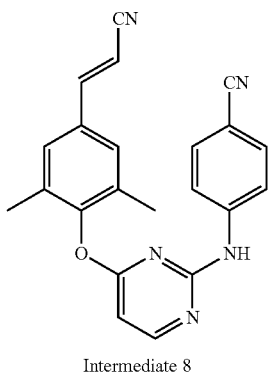

Intermediate 7

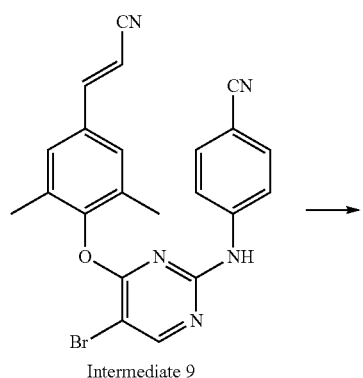

Intermediate 8

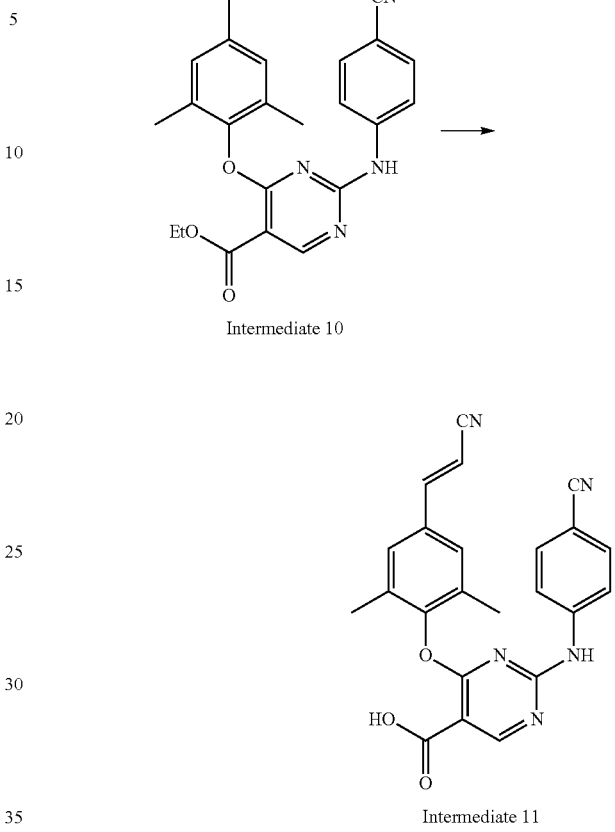

Intermediate 9

Intermediate 10

Intermediate 11

Sodium hydride (60% in oil, 0.036 mol, 1.1 eq.) was added to a stirred solution of 2,6-dimethyl-4-hydroxy-benzaldehyde (0.033 mol, 1.1 eq.) in dioxane (50 ml). Stirring was continued for 10 min before adding 1-methyl-2-pyrrolidinone (50 ml). After another 10 min, intermediate 2 (0.033 mol) was added and the whole mixture was heated at reflux for 18 hours. After cooling down, water and ice were added. The pure product was obtained by filtration. Yield 11.2 g (98%) of Intermediate 7.

Potassium tertbutoxyde (0.026 mol, 1.5 eq.) was added to a solution of diethyl-phosphonoacetonitrile (0.026 mol, 1.5 eq.) in THF (60 ml) at 5° C. under nitrogen. Stirring was maintained 60 min before intermediate 7 (0.017 mol) was added and the whole mixture was stirred 12 hours at room temperature. After cooling down, water was added and the extraction conducted with dichloromethane. The organic layer was dried over magnesium sulfate, filtered and the solvent evaporated. The pure product was obtained by crystallization in ether of the crude. Yield 3.6 g (56%) of Intermediate 8.

Intermediates 9, 10 and 11 were prepared following the same procedures as those previously described in examples 1-4.

Example 7

Following the procedures of example 5 or 6 the following compounds were prepared:

TABLE 2

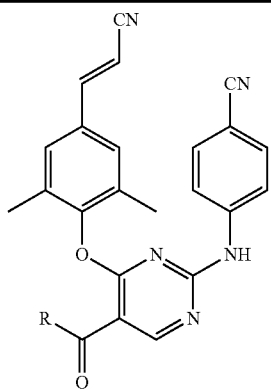

| Compound No. | R | Phys. Data and stereo-chemistry |
|---|---|---|
| 58 | (4-pyridyl-CH2-NH-) | (E) >250° C. Yield 62% |
| 59 | (tetrahydrofuran-2-yl-CH2-NH-) | (E) 118° C. Yield 53% |
| 60 | (CH3-O-CH2-CH2-NH-) | (E) 134° C. Yield 57% |
| 61 | (NC-CH2-NH-) | (E) >250° C. Yield 53% |
| 62 | (CH3-O-NH-) | (E) 132° C. Yield 55% |

Formulation Examples

Capsules

A compound of formula (I) is dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxyl-propylmethylcellulose (HPMC), typically 5 mPa·s, are dissolved in organic solvents such as ethanol, methanol methylene chloride. Suitably the polymer is dissolved in ethanol. The polymer and compound solutions are mixed and subsequently spray dried. The ratio of compound/polymer is selected from 1/1 to 1/6. Intermediate ranges can be 1/1.5 and 1/3. A suitable ratio can be 1/6. The spray-dried powder, a solid dispersion, is subsequently filled in capsules for administration. The drug load in one capsule ranges between 50 and 100 mg depending on the capsule size used.

Film-Coated Tablets
Preparation of Tablet Core

A mixture of 100 g of a compound of formula (I), 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinyl-pyrrolidone and 30 ml of concentrated color suspension and the whole is homogenized. The tablet cores are coated with the thus obtained mixture in a coating apparatus.

Antiviral Spectrum:

Because of the increasing emergence of drug resistant HIV strains, the present compounds were tested for their potency against clinically isolated HIV strains harbouring several mutations. These mutations are associated with resistance to reverse transcriptase inhibitors and result in viruses that show various degrees of phenotypic cross-resistance to the currently commercially available drugs such as for instance AZT and delavirdine.

The antiviral activity of the compound of the present invention has been evaluated in the presence of wild type HIV and HIV mutants bearing mutations at the reverse transcriptase gene. The activity of the compounds is evaluated using a cellular assay which was performed according to the following procedure.

The human T-cell line MT4 is engineered with Green Fluorescent Protein (GFP) and an HIV-specific promoter, HIV-1 long terminal repeat (LTR). This cell line is designated MT4 LTR-EGFP, and can be used for the in vitro evaluation of anti-HIV activity of investigational compounds. In HIV-1 infected cells, the Tat protein is produced which upregulates the LTR promoter and finally leads to stimulation of the GFP reporter production, allowing to measure ongoing HIV-infection fluorometrically. Analogously, MT4 cells are engineered with GFP and the constitutional cytomegalovirus (CMV) promoter. This cell line is designated MT4 CMV-EGFP, and can be used for the in vitro evaluation of cytotoxicity of investigational compounds. In this cell line, GFP levels are comparably to those of infected MT4 LTR-EGFP cells. Cytotoxic investigational compounds reduce GFP levels of mock-infected MT4 CMV-EGFP cells.

Effective concentration values such as 50% effective concentration (EC50) can be determined and are usually expressed in μM. An EC50 value is defined as the concentration of test compound that reduces the fluorescence of HIV-infected cells by 50%. The 50% cytotoxic concentration (CC50 in μM) is defined as the concentration of test compound that reduces fluorescence of the mock-infected cells by 50%. The ratio of CC50 to EC50 is defined as the selectivity index (SI) and is an indication of the selectivity of the anti-HIV activity of the inhibitor. The ultimate monitoring of HIV-1 infection and cytotoxicity is done using a scanning microscope. Image analysis allows very sensitive detection of viral infection. Measurements are done before cell necrosis, which usually takes place about five days after infection, in particular measurements are performed three days after infection.

The columns IIIB, L100I, etc. in the table list the $pEC_{50}$ values against various strains IIIB, L100I, etc.

Strain IIIB is wild type HIV strain

MDR refers to a strain that contains mutations L100I, K103N, Y181C, E138G, V179I, L2214F, V278V/I and A327A/V in HIV reverse transcriptase.

| Co. No | IIIB pEC$_{50}$ | C | pSi | L100I pEC$_{50}$ | K103N pEC$_{50}$ | L100I + K103N pEC$_{50}$ | Y181C pEC$_{50}$ | K103N + Y181C pEC$_{50}$ | Y188L pEC$_{50}$ | MDR pEC$_{50}$ |
|---|---|---|---|---|---|---|---|---|---|---|
| 22 | 9.10 | | 3.90 | 7.70 | 7.00 | 9.20 | 7.70 | 7.80 | 7.30 | 5.70 |
| 38 | 9.10 | | 3.70 | 7.60 | 7.20 | 9.00 | 7.80 | 7.70 | 7.60 | 5.70 |
| 55 | 9.00 | | 4.00 | 7.80 | 7.10 | 8.40 | 7.00 | 7.70 | 7.20 | 5.70 |
| 12 | 8.90 | | 4.10 | 8.60 | 7.70 | 8.60 | 7.90 | 7.80 | 8.00 | 6.00 |
| 6 | 8.80 | > | 4.20 | 6.80 | 5.90 | 8.30 | 6.40 | 7.00 | 6.50 | 5.00 |
| 7 | 8.80 | | 4.00 | 8.10 | 7.30 | 8.70 | 7.20 | 7.70 | 7.30 | 5.70 |
| 3 | 8.70 | | 4.00 | 8.30 | 7.90 | 8.50 | 7.20 | 7.80 | 7.60 | 5.60 |
| 11 | 8.70 | | 3.40 | 8.10 | 7.30 | 8.40 | 7.10 | 7.40 | 7.60 | 5.80 |
| 44 | 8.70 | > | 4.10 | 7.90 | 7.50 | 8.60 | 8.00 | 8.00 | 8.10 | 5.90 |
| 9 | 8.60 | > | 4.00 | 8.30 | 7.60 | 8.50 | 7.70 | 7.90 | 7.80 | 6.00 |
| 10 | 8.60 | > | 4.00 | 8.40 | 7.40 | 8.50 | 7.20 | 7.80 | 7.70 | 6.30 |
| 14 | 8.60 | > | 4.00 | 8.60 | 7.80 | 8.60 | 8.00 | 7.90 | 7.90 | 6.20 |
| 54 | 8.60 | > | 4.00 | 8.40 | 7.80 | 8.70 | 7.90 | 8.00 | 8.00 | 6.00 |
| 37 | 8.60 | | 3.60 | 8.30 | 7.70 | 8.80 | 8.10 | 7.90 | 7.90 | 6.00 |
| 45 | 8.60 | > | 4.00 | 8.20 | | 8.70 | 7.80 | | 7.70 | 6.00 |
| 2 | 8.50 | > | 3.90 | 7.20 | 6.70 | 7.90 | 6.30 | 6.90 | 6.40 | 5.00 |
| 53 | 8.50 | > | 3.90 | 8.30 | 7.60 | 8.20 | 7.50 | 7.70 | 7.50 | 6.30 |
| 15 | 8.50 | | 3.70 | 7.90 | 7.20 | 8.50 | 7.70 | 7.80 | 7.70 | 6.70 |
| 19 | 8.40 | | 3.60 | 8.40 | 7.30 | 8.40 | 7.70 | 7.70 | 7.70 | 6.00 |
| 23 | 8.40 | > | 3.80 | 8.30 | 7.90 | | 8.10 | 7.80 | 7.80 | 6.10 |
| 51 | 8.40 | | 3.00 | 7.10 | 6.90 | 8.20 | 7.20 | 7.20 | 7.00 | 5.60 |
| 5 | 8.30 | > | 3.70 | 7.60 | 7.30 | 8.00 | 6.80 | 7.00 | 7.00 | 5.40 |
| 20 | 8.30 | | 3.60 | 7.80 | 7.00 | 8.30 | 7.50 | 7.40 | 7.30 | 5.60 |
| 41 | 8.30 | > | 3.70 | 8.10 | 7.30 | 8.40 | 7.70 | 7.80 | 7.10 | 5.80 |
| 27 | 8.20 | > | 3.60 | 7.30 | | 8.10 | 7.40 | 7.40 | 7.10 | 5.50 |
| 46 | 8.10 | > | 3.50 | 8.10 | 7.80 | 8.40 | 7.40 | | 7.50 | 6.80 |
| 26 | 7.90 | | 3.00 | 7.60 | 6.50 | 7.90 | 7.40 | 7.30 | 7.10 | 5.30 |
| 25 | 7.90 | | 3.00 | 7.60 | 7.40 | 7.80 | 7.50 | 7.10 | 7.30 | 5.00 |
| 32 | 7.90 | | 3.10 | 7.40 | | 7.80 | 7.10 | 7.10 | 7.00 | 5.00 |
| 30 | 7.90 | > | 3.30 | 7.00 | 6.60 | 7.80 | 7.00 | 7.00 | 6.50 | 5.30 |
| 43 | 7.90 | > | 3.30 | 7.30 | 6.90 | 8.00 | 7.10 | 7.60 | 7.10 | 5.50 |
| 21 | 7.80 | | 2.80 | 8.40 | 7.80 | 8.30 | 7.80 | 7.80 | 7.80 | 6.30 |
| 24 | 7.80 | | 3.00 | 7.60 | 7.10 | | 7.30 | 7.60 | 7.10 | 5.30 |
| 31 | 7.80 | | 3.10 | 7.50 | | 7.80 | 7.30 | 7.20 | 7.10 | 5.00 |
| 28 | 7.80 | | 3.10 | 7.30 | | 7.80 | 7.30 | 7.10 | 6.90 | 5.10 |
| 29 | 7.80 | | 3.00 | 7.10 | 6.90 | 7.70 | 7.00 | 7.10 | 6.80 | 5.00 |
| 33 | 7.80 | > | 3.20 | 7.80 | 7.80 | 7.80 | 7.90 | 7.30 | 7.20 | 6.40 |
| 49 | 7.80 | | 3.00 | 7.70 | 7.20 | 7.80 | 7.30 | 7.10 | 7.10 | 6.30 |
| 47 | 7.70 | | 3.10 | 7.20 | 6.90 | 7.60 | 6.90 | 7.30 | 7.00 | 6.30 |
| 48 | 7.70 | | 3.10 | 6.90 | 6.30 | 7.70 | 6.70 | 6.90 | 6.50 | 5.00 |
| 16 | 7.60 | | 2.60 | 7.10 | 6.30 | 8.40 | 6.50 | 6.70 | 6.30 | 5.10 |
| 36 | 7.60 | > | 3.00 | 6.90 | 6.10 | 7.60 | 6.90 | 6.90 | 6.40 | 5.00 |
| 58 | 8.70 | > | 4.10 | | 6.50 | 8.20 | 7.00 | | 6.80 | 5.50 |
| 59 | 8.60 | | 3.80 | 7.20 | 6.60 | 8.20 | 7.10 | 7.50 | 6.60 | 5.40 |
| 60 | 8.50 | | 3.50 | 7.10 | 6.50 | 7.90 | 7.20 | 7.50 | 6.80 | 5.00 |
| 61 | 8.50 | > | 3.90 | 7.70 | 7.30 | 8.40 | 7.60 | 7.70 | 7.00 | 5.50 |
| 62 | 8.80 | | 4.00 | 8.30 | 7.40 | 8.60 | 7.50 | 7.70 | 7.40 | 5.50 |

The invention claimed is:

1. A compound having the following structure:

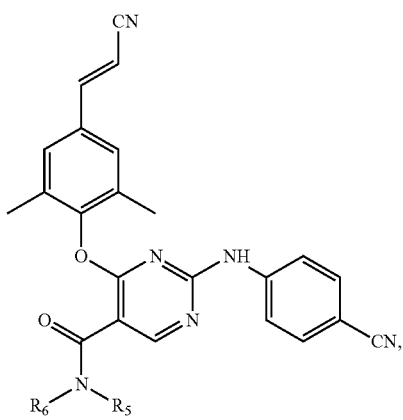

wherein:

R$^5$ is selected from C$_{3-7}$cycloalkyl; C$_{1-6}$alkyloxy; aryl; Het; C$_{1-6}$alkyl substituted with a radical selected from hydroxy, C$_{1-6}$alkyloxy, cyano, amino, mono- and di-C$_{1-6}$ alkylamino, C$_{1-6}$alkylcarbonylamino, aryl, Het, dioxolanyl optionally substituted with one or two C$_{1-6}$alkyl radicals, tetrahydrofuranyl, pyrrolidinyl, piperidinyl, morpholinyl, piperazinyl, piperazinyl optionally substituted with C$_{1-6}$alkyl or C$_{1-6}$alkylcarbonyl, C$_{1-6}$alkyloxycarbonyl, arylC$_{1-6}$alkyloxycarbonyl, or C$_{3-7}$cycloalkyl; and is C$_{1-6}$alkyl substituted with two C$_{1-6}$alkyloxy radicals;

R$^6$ is selected from hydrogen and C$_{1-6}$alkyl; or

R$^5$ and R$^6$ taken together with the nitrogen atom to which they are attached form pyrrolidinyl; piperidinyl; morpholinyl; piperazinyl; or piperazinyl optionally substituted with C$_{1-6}$alkyl or C$_{1-6}$alkylcarbonyl.

2. A compound according to claim 1, wherein:

R$^5$ is C$_{3-7}$cycloalkyl; C$_{1-6}$alkyloxy; aryl; Het; C$_{1-6}$alkyl substituted with a radical selected from hydroxy, C$_{1-6}$alkyloxy, cyano, di-C$_{1-6}$alkylamino, C$_{1-6}$alkylcarbonyl amino, aryl, Het, dioxolanyl substituted with two $C_{1-6}$alkyl radicals, tetrahydrofuranyl, pyrrolidinyl, $C_{1-6}$alkyloxycarbonyl, and $C_{3-7}$cycloalkyl;

$R^6$ is hydrogen or $C_{1-6}$alkyl; or $R^5$ and $R^6$ taken together with the nitrogen atom to which they are substituted form morpholinyl; piperazinyl substituted with $C_{1-6}$alkyl.

3. A compound according to claim 1, wherein $R^5$ is $C_{3-7}$cycloalkyl; $C_{1-6}$alkyloxy; $C_{1-6}$alkyl substituted with a radical selected from hydroxy, $C_{1-6}$alkyloxy, cyano, $C_{1-6}$alkylcarbonylamino, aryl, Het, $C_{1-6}$alkyloxycarbonyl; and $R^6$ is hydrogen.

4. A compound according to claim 1, wherein each Het independently is pyridyl, thienyl, thiazolyl, furanyl, each of which may be optionally substituted with a radical selected from $C_{1-6}$alkyl.

5. A compound according to claim 1, wherein each aryl independently may be phenyl optionally substituted with $C_{1-6}$alkylamino, mono- or di-$C_{1-6}$alkyl-amino, $C_{1-6}$alkyloxy, aminosulfonyl, Het, the latter more in particular being thiadiazolyl.

6. A pharmaceutical composition comprising a pharmaceutically acceptable carrier and as active ingredient a therapeutically effective amount of a compound as claimed in claim 1.

7. A compound according to claim 1, having the following structure:

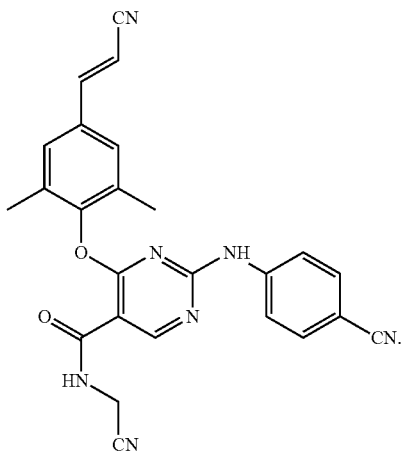 [SMILES: Cc1cc(/C=C/C#N)cc(C)c1Oc1nc(Nc2ccc(C#N)cc2)ncc1C(=O)NCC#N]

8. A compound according to claim 1, having the following structure:

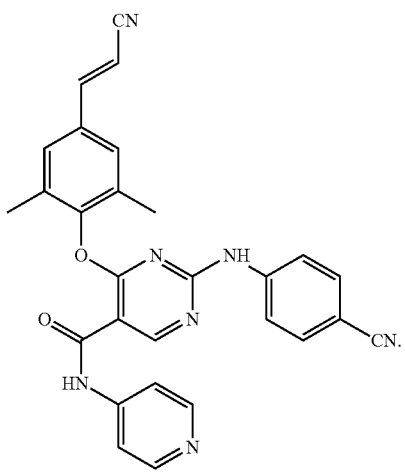 [SMILES: Cc1cc(/C=C/C#N)cc(C)c1Oc1nc(Nc2ccc(C#N)cc2)ncc1C(=O)Nc1ccncc1]

9. A compound according to claim 1, having the following structure:

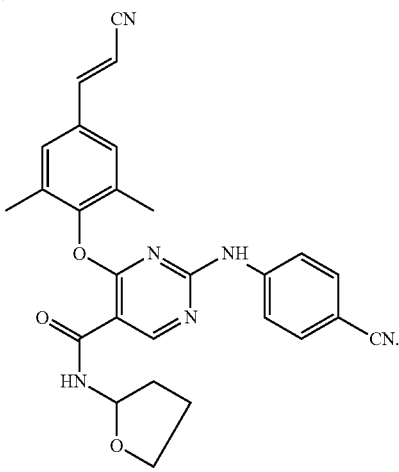 [SMILES: Cc1cc(/C=C/C#N)cc(C)c1Oc1nc(Nc2ccc(C#N)cc2)ncc1C(=O)NC1CCCO1]

10. A compound according to claim 1, having the following structure:

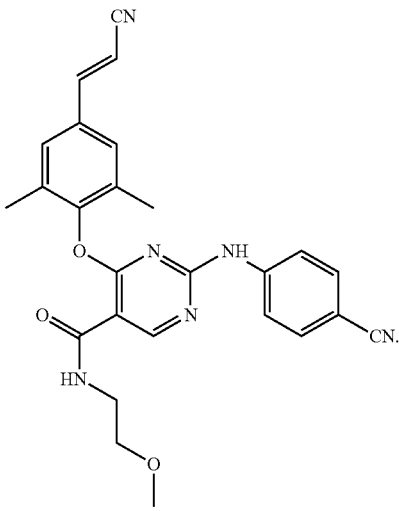 [SMILES: COCCNC(=O)c1cnc(Nc2ccc(C#N)cc2)nc1Oc1c(C)cc(/C=C/C#N)cc1C]

11. A compound according to claim 1, having the following structure:

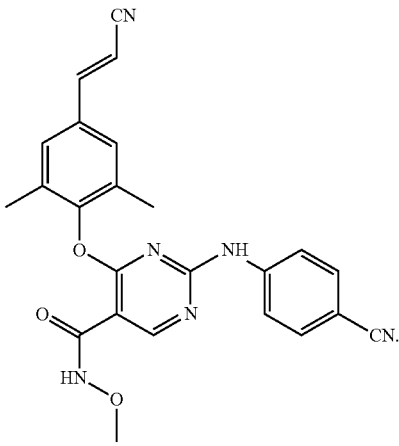 [SMILES: CONC(=O)c1cnc(Nc2ccc(C#N)cc2)nc1Oc1c(C)cc(/C=C/C#N)cc1C]

* * * * *